United States Patent

Rossey

[11] 4,316,029
[45] Feb. 16, 1982

[54] SYNTHESIS OF VINCAMINIC ACID DERIVATIVES

[75] Inventor: Guy Rossey, Cachan, France
[73] Assignee: Synthelabo, Paris, France
[21] Appl. No.: 161,359
[22] Filed: Jun. 20, 1980

[30] Foreign Application Priority Data

Jun. 22, 1979 [FR] France ................ 79 16030

[51] Int. Cl.³ .................................... C07D 461/00
[52] U.S. Cl. ......................... 546/51; 546/70
[58] Field of Search .................. 546/51, 70; 424/256

[56] References Cited

U.S. PATENT DOCUMENTS

| | | | |
|---|---|---|---|
| 3,755,333 | 8/1973 | Szantay et al. | 546/51 |
| 3,987,049 | 10/1976 | Plat et al. | 546/51 |
| 4,033,969 | 7/1977 | Sevenet et al. | 546/51 |
| 4,117,133 | 9/1978 | Bonati et al. | 546/78 |

FOREIGN PATENT DOCUMENTS

| | | | |
|---|---|---|---|
| 2317304 | 2/1977 | France | 546/51 |
| 473701 | 4/1979 | Spain . | |

OTHER PUBLICATIONS

Montoro, et al., Chemical Abstracts, 89, 180220r (1978).

Fieser, et al., "Advanced Organic Chemistry," Reinhold Publishing Corp., New York (1961), p. 378.

*Primary Examiner*—Donald G. Daus
*Assistant Examiner*—Diana G. Rivers
*Attorney, Agent, or Firm*—Wegner & Bretschneider

[57] ABSTRACT

Vincaminic acid derivatives of formula (A)

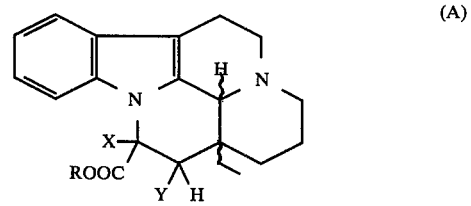

useful in treating cerebral insufficiency, are prepared by reacting 1-ethyl-2,3,4,6,7,12-hexahydroindolo[2,3-a]quinolizine with the 2,4-DNP hydrazone of ethyl or methyl bromopyruvate followed by (i) reduction of the C=N bond and (ii) simultaneous cyclization with removal of the ketone-protecting group in either order.

7 Claims, No Drawings

SYNTHESIS OF VINCAMINIC ACID DERIVATIVES

DESCRIPTION

The present invention relates to a new synthesis of vincaminic acid derivatives, in particular of vincamine, apovincamine and deoxyvincamine and of the ethyl esters of vincaminic acid, apovincaminic acid and deoxyvincaminic acid, in the form of racemates and enantiomers.

Several syntheses of vincamine have already been described in the literature; these are either partial syntheses starting from natural alkaloids (for example from tabersonine, French Pat. No. 71/47,731), or total syntheses (French Pat. No. 70/11,406 and U.S. Pat. No. 3,454,583).

Vincamine is known for its valuable pharmacological properties as a cerebral oxygenating agent and cerebral vasoregulator and for its therapeutic activity for the treatment of cerebral insufficiencies.

The synthesis of the invention is carried out starting from 1-ethyl-2,3,4,6,7,12-hexahydroindolo[2,3-a]quinolizine,

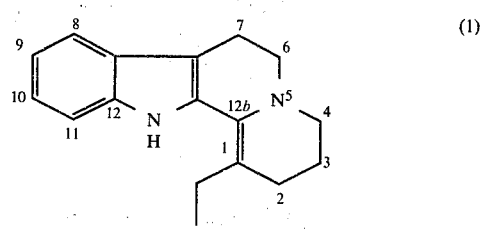

this product being described by WENKERT and WICKBERG (J.Am.Chem.Soc. 87, 1,580 (1965)).

Scheme (1) for the synthesis of vincamine and scheme (2) for the synthesis of deoxyvincamine and apovincamine are shown on the following pages.

Scheme 1

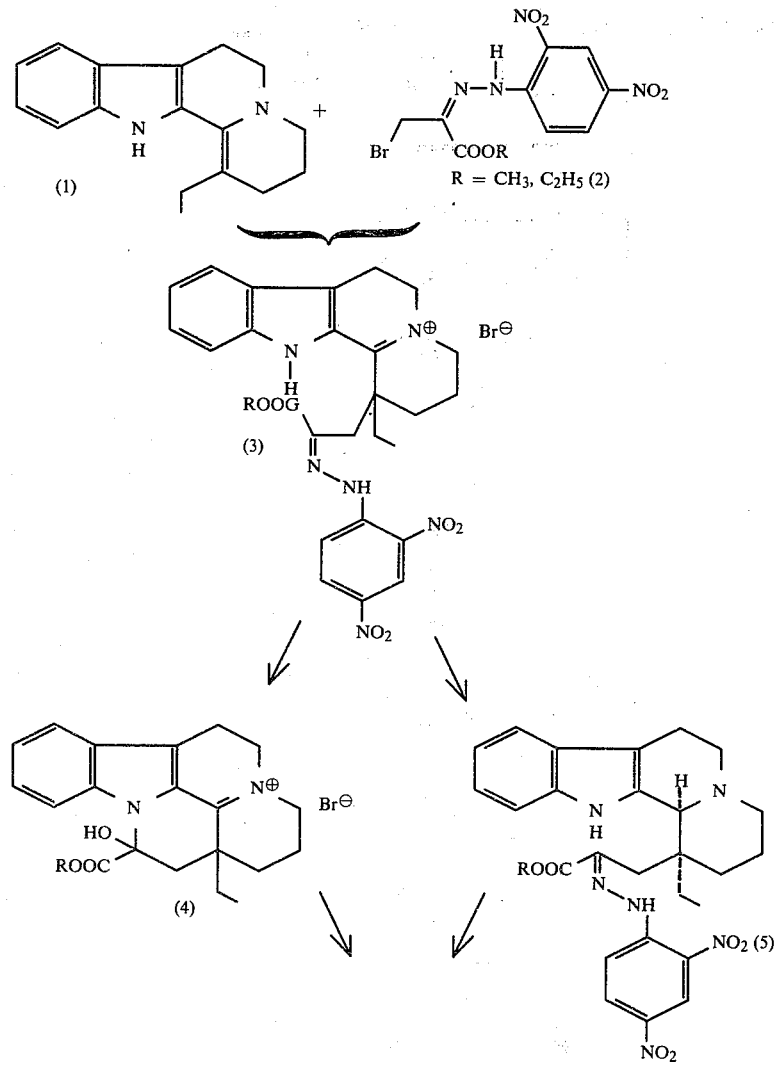

-continued
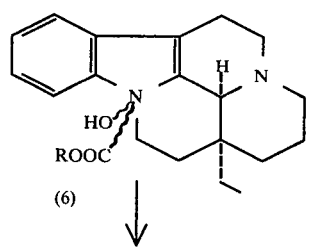
(6)
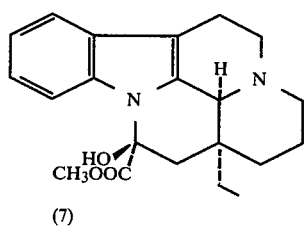
(7)
Scheme 2
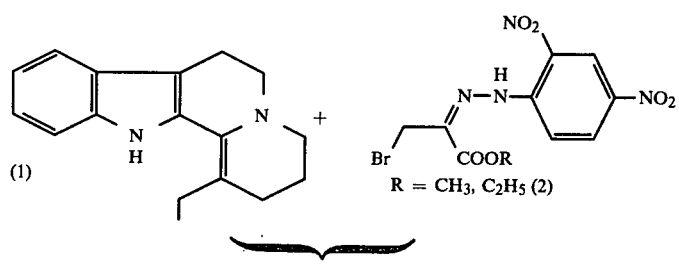
(1)    R = CH₃, C₂H₅ (2)
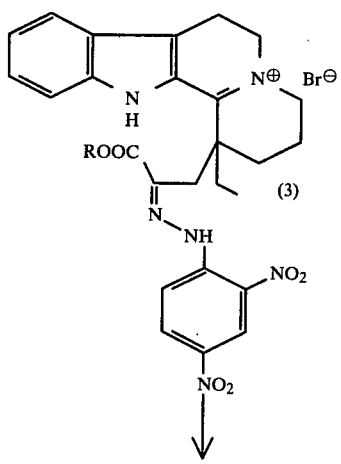
(3)
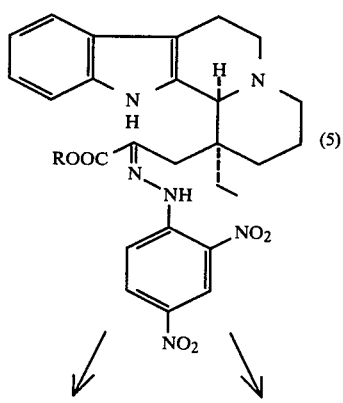
(5)

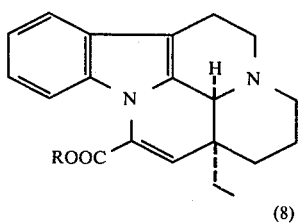
(8)

-continued

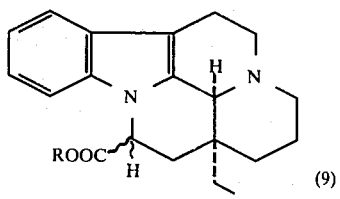
(9)

To prepare vincamine according to the invention, the enamine (1) is reacted with the (2,4-dinitrophenyl)-hydrazone of methyl or ethyl bromopyruvate (2), and then either the protective group is removed from the compound (3) in order to obtain the cyclised compound (4), which is reduced in order to obtain the cyclised compound (6), or the compound (3) is reduced in order to obtain the compound (5), from which the protective group is removed in order to obtain the cyclised compound (6), and, if appropriate, the compound (6) is transesterified (if it is the ethyl ester) to give (±)-vincamine (7).

The first step can be carried out in a solvent, such as ethyl acetate, at ambient temperature. The removal of the protective group from the compound (3) to give the compound (4) can be carried out in a solvent such as a mixture of acetonitrile and water, adjusted to a suitable pH, e.g. about pH 8, using preferably sodium borate and hydrochloric acid. Ambient temperature can be used in this step also.

The reduction of the compound (4) can be carried out by any suitable means, such as zinc in the presence of 50% strength acetic acid or Raney nickel in 50% strength acetic acid.

The reduction of the compound (3) to give the compound (5) can be carried out, for example, by means of an alkali metal hydride in an acid medium in a solvent, such as methanol or acetronitrile, or a mixture thereof.

The removal of the protective group from the compound (5) is carried out by means of titanium (III) chloride in a solvent, such as methanol or acetonitrile, containing formaldehyde and an acid, such as hydrochloric acid or acetic acid, in a temperature range of 20° to 140° C.

If appropriate, the transesterification of the compound (6) to give (±)-vincamine (7) is carried out by heating in methanol at the reflux temperature, in the presence of sodium methylate.

The cis-vincamine obtained according to the synthesis of the invention is in the (±) racemic form. The compound (5) is obtained directly in the cis form, starting from the compound (3), in a proportion of at least 80%.

The compound (6) is a mixture of the two epimers on the carbon in the 14-position, the H-atom in the 3-position and the ethyl in the 16-position being in the cis position, relative to each other.

To prepare apovincamine and deoxyvincamine according to the invention, the enamine (1) is reacted with the (2,4-dinitrophenyl)-hydrazone of ethyl or methyl bromopyruvate (2), and the compound (3) is then reduced to give the compound (5), which is reacted, in formic acid, either with an approx. 15% aqueous solution of titanium (III) chloride in order to obtain ethyl apovincaminate (8,R=C$_2$H$_5$) or apovincamine (8,R=CH$_3$), or with an approx. 30% aqueous solution of titanium (III) chloride in order to obtain ethyl deoxyvincaminate (9, R=C$_2$H$_5$) or deoxyvincamine (9, R=CH$_3$). The strengths of the solutions are weight-/volume.

The vincamine obtained in accordance with reaction scheme 1 is cis-vincamine in the (±) racemic form. Now, the Applicant Company has succeeded in resolving the compound (5) (itself also in the racemic form) in order to obtain the dextrorotatory and laevorotatory enantiomers and to lead directly, starting from this compound, to optically active vincaminic acid derivatives, especially cis-(+)-vincamine and cis-(−)-vincamine.

According to the invention, the resolution of the compound (5) is carried out using an optically active acid, such as dibenzoyl-L-tartaric acid, in a solvent, such as acetonitrile.

The following examples illustrate the invention.

The analyses and the IR and NMR spectra confirmed the structure of the compounds.

The starting compound (2) is new. If R is C$_2$H$_5$, it is obtained in the following manner:

39 g (0.2 mol) of ethyl bromopyruvate are added to 41 g (0.2 mol) of (2,4-dinitrophenyl)-hydrazine in an acid, such as hydrochloric or acetic acid. The temperature is allowed to return to 20° C. and the precipitate formed is filtered off, washed copiously with water and then dried in vacuo at 60° C.

60 g of ethyl [2-(2,4-dinitrophenyl)-hydrazono-3-bromopyruvate] are obtained.

Melting point=150.5° C.

Methyl [2-(2,4-dinitrophenyl)-hydrazono-3bromopyruvate] is prepared in the same manner.

Melting point=158° C.

EXAMPLE 1

(±)-Vincamine (Scheme 1. R=C$_2$H$_5$).

1.

1-[2-(2,4-Dinitrophenyl)-hydrazono-2-ethoxycarbonylethyl]-1-ethyl-1,2,3,4,6,7-hexahydro-(12H)-indolo[2,3-a]-quinolizin-5-ium bromide (compound 3)

29 g (77.35 mmols) of the starting compound (2) are dissolved in 1.7 liters of ethyl acetate. 8.95 g (88.6 mmols) of triethylamine, dried over KOH, are added to the solution, whilst stirring, and a solution of 15.7 g (62.4 mmols) of the enamine (1) in 500 ml of ethyl acetate is then added. The reaction mixture is stirred at ambient temperature overnight. The precipitate formed is filtered off and washed with ethyl acetate. The resulting product is dried in vacuo at 40° C. This yields 39 g (yield 99.6%) of an orange powder which melts at 200° C. with decomposition.

2. Ethyl dehydrovincaminate chloride (compound 4)

1.56 g (2.48 mmols) of the compound (3) obtained above are dissolved in 50 ml of acetonitrile. 150 ml of water are added and 50 ml of a buffer at pH 8, consisting of a concentrated solution of sodium borate and hydrochloric acid, are then added. The reaction mixture is stirred overnight. The small amount of precipitate formed is filtered off. The aqueous phase is washed three times with 50 ml of toluene and extracted with methylene chloride. The organic phase is dried over sodium sulphate and filtered and the filtrate is concentrated. This yields 1 g (yield 100%) of the compound (4), which is used as such for the following step.

3. (±)-Vincamine 1 g (2.48 mmols) of the compound (4) obtained above is dissolved in 65 ml of 50% strength acetic acid. The solution is heated to 88° C. in the course of 4 minutes and 5 g of zinc are then added in small amounts. Heating is maintained for 5 minutes. The reaction mixture is poured onto 65 g of ice and treated with 50 ml of 28% strength ammonia solution. The precipitate is filtered off and dried in vacuo at 60° C. This yields 0.55 g of the compound (6), which is taken up in 3 ml of methanol. The mixture is heated at the reflux temperature, in the presence of sodium methylate (0.1 ml of a 30% strength solution in methanol), for 5 hours. This yields 0.33 g (yield 38%) of (±)-vincamine.

EXAMPLE 2

(±)-Vincamine (Scheme 1. R=$C_2H_5$).

1. The compound (3) is prepared as in Example 1

2. 1-[2-(2,4-Dinitrophenyl)-hydrazono-2-ethoxycarbonylethyl]-1-ethyl-1,2,3,4,6,7,12,12b-octahydroindolo[2,3a]-quinolizine 10.5 g (167 mmols) of $NaBH_3CN$ are added, whilst stirring, to a solution of 35 g of the compound (3) in 40 ml of acetic acid, 200 ml of methanol, 200 ml of acetonitrile and 200 ml of water. After one hour at ambient temperature, the solution is treated with 80 ml of 28% strength ammonia solution and 200 ml of water. The aqueous phase is extracted with methylene chloride. The organic phases are concentrated and the residue is taken up in 150 ml of methanol. The mixture is heated at the reflux temperature for 15 minutes, left to cool and filtered.

This yields 24.57 g (yield 80%) of compound (5) melting at 214° C.

3. Ethyl (±)-vincaminate 1 g (1.82 mmols) of the compound (5) obtained above is dissolved in 20 ml of acetone and 10 ml of acetic acid. The solution is degassed with argon and added, in the course of 2 minutes, to a solution, kept at 67° C., containing 30 ml of a 15% strength solution of titanium chloride in water, 30 ml of a 37% strength solution of formaldehyde in degassed water, and 10 ml of degassed acetic acid.

After a reaction time of 20 minutes at 67° C., 200 ml of iced water are added to the reaction mixture and the resulting mixture is extracted with methylene chloride. The combined organic phases are concentrated. The residue is taken up in 30 ml of iced water. The resulting solution is treated with 28% strength ammonia solution. The mixture is filtered and the precipitate is dried at 60° C. in vacuo. This yields 0.460 g (68%) of a mixture of epimers (in the 14-position) of the compound (6).

4. (±)-Vincamine

A solution of the compound (6) in methanol is heated at the reflux temperature for 5 hours in the presence of sodium methylate. This yields 0.326 g of (±)-vincamine.

Spectrographic analysis

NMR: ($CDCl_3$, DMSO): 0.95 (t,3H), 1.40 (m,6H), 2.60 (m,3H), 3.30 (m,2H), 3.78 (s,3H), 3.86 (broad s, 1H), 7.07 (m,3H), 7.36 (m,1H).

IR: (KBr,cm$^{-1}$): 3,440 (OH, broad), 2.920 (m), 2,840 (sh), 1,730 (COOMe).

EXAMPLE 3

(±)-Vincamine (Scheme 1. R=$CH_3$)

1. A solution containing 6.88 g (27 mM) of enamine and 2.9 g (29 mM) of triethylamine in 60 ml of ethyl acetate is added to a suspension of 10 g (29 mM) of the (2,4-dinitrophenyl)-hydrazone of methyl bromopyruvate in 140 ml of ethyl acetate. The mixture is stirred for 16 hours and filtered and the product is washed with ethyl acetate. It is dried in vacuo at 70° C. This yields 15.2 g of 1-[2-(2,4-dinitrophenyl)-hydrazono-2-methoxycarbonylethyl]-1-ethyl-1,2,3,4,6,7-hexahydro-(12H)-indolo[2,3-a]quinolizin-5-ium bromide. (Yield: 92%).

Melting point=205° C. (decomposition).

2. 4.9 g (7.98 mM) of the latter compound are reduced with 1.29 g (24 mM) of potassium borohydride in order to obtain 1-[2-(2,4-dinitrophenyl)-hydrazono-2-methoxycarbonylethyl]-1-ethyl-1,2,3,4,6,7,12,12b-octahydroindolo[2,3-a]quinolizine (3.6 g; yield: 74%).

Melting point=205°-206° C.

3. 2 g (2.74 mM) of the product obtained above, in 28 ml of acetone, are added to a solution, at 55°-60° C., containing 60 ml of acetone, 10 ml of a 37% strength aqueous solution of formaldehyde, 20 ml of acetic acid and 60 ml of titanium (III) chloride solution (15% strength). The reaction is kept at 60° C. for 15 minutes and ice is then added. 5 g (72 mM) of $NaNO_2$ are added and nitrogen is bubbled for 15 minutes. Extraction is carried out with methylene chloride, the organic phase is concentrated and the residue is taken up in 10 ml of water. The solution is rendered basic with ammonia and filtered and the (±)-vincamine is dried (0.974 g; yield: 74%).

Melting point=242° C. (MeOH).

EXAMPLE 4

Ethyl (±)-apovincaminate 1. 1-[2-(2,4-Dinitrophenyl)-hydrazono-2-ethoxycarbonylethyl]-1-ethyl-1,2,3,4,6,7-hexahydro-(12H)-indolo]2,3-a]-quinolizin-5-ium bromide (compound 3)

29 g (77.35 mmols) of the starting compound (2) are dissolved in 1.7 liters of ethyl acetate. 8.95 g (88.6 mmols) of triethylamine, dried over KOH, are added to the solution, whilst stirring, and a solution of 15.7 g (62.4 mmols) of the enamine (1) in 500 ml of ethyl acetate is then added. The reaction mixture is stirred at ambient temperature overnight. The precipitate formed is filtered off and washed with ethyl acetate. The resulting product is dried in vacuo at 40° C. This yields 39 g (yield 99.6%) of an orange powder which melts at 200° C. with decomposition.

2.

(±)-1-[2-(2,4-Dinitrophenyl)-hydrazono-2-ethoxycarbonylethyl]-1-ethyl-1,2,3,4,6,7,12,12b-octahydroindolo]2,3-a]quinolizine 10.5 g (167 mmols) of NaBH$_3$CN are added, whilst stirring, to a solution of 35 g of compound (3) in 40 ml of acetic acid, 200 ml of methanol, 200 ml of acetonitrile and 200 ml of water. After one hour at ambient temperature, the solution is treated with 80 ml of 28% strength ammonia solution and 200 ml of water. The aqueous phase is extracted with methylene chloride. The organic phases are concentrated and the residue is then taken up in 150 ml of methanol. The mixture is heated at the reflux temperature for 15 minutes, left to cool and filtered.

This yields 24.57 g (yield 80%) of compound (5) melting at 214° C.

3. Ethyl (±)-apovincaminate 2.5 g (4.5 mmols) of the compound obtained above, in 75 ml of formic acid, are heated to the reflux temperature and 60 ml of 15% strength solution of titanium (III) chloride are added. The reaction mixture is heated for 20 minutes under reflux and ice is then added. The titanium dioxide is removed by filtration and the product is extracted with methylene chloride. The organic phases are washed with ammonia solution and then with water and are then dried over sodium sulphate. The solvent is removed and the solid residue is recrystallised from petroleum ether. This yields 1.24 g of ethyl apovincaminate in the form of a pale yellow solid.

Melting point = 122° C.

(±)-Apovincamine can be prepared in the same manner starting from the compound (3) obtained from methyl bromopyruvate and the enamine (1).

EXAMPLE 5

Ethyl (±)-deoxyvincaminate

A solution of 5 g (9 mmols) of the compound obtained in Example 4, paragraph 1, in 150 ml of formic acid is heated to the reflux temperature and 125 ml of a 30% strength solution of titanium (III) chloride are added. Reflux is maintained for 20 minutes. Ice is added to the reaction mixture and the precipitate of titanium dioxide is removed by filtration. The product is extracted from the filtrate with methylene chloride and the organic phase is washed with ammonia solution and water. After drying over sodium sulphate and removing the solvent, a viscous oil (3.2 g) is obtained, which consists solely of a mixture of the two C$_{14}$ epimers of ethyl deoxyvincaminate (spectral and chromatographic data are in agreement) (yield: 100%).

(±)-Deoxyvincamine can be prepared in the same manner starting from methyl bromopyruvate and the enamine (1).

EXAMPLE 6

(+)-Vincamine and (−)-Vincamine

1.

(+)-1β-[2-(2,4-Dinitrophenyl)-hydrazono-2-methoxycarbonylethyl]-1α-ethyl-1,2,3,4,6,7,12,12bα-octahydroindolo[2,3-a]quinolizine and (−)-1α-[2-(2,4-dinitrophenyl)-hydrazono-2-methoxycarbonylethyl]-1β-ethyl-1,2,3,4,6,7,12,12bβ-octahydroindolo[2,3-a]quinolizine 100 ml (0.0187 mM) of the compound (5) and 70 mg of dibenzoyl-L-tartaric acid in 3 ml of CH$_3$CN are heated to the reflux temperature. After cooling, the crystals formed are filtered off and washed with acetonitrile (1 ml). The filtrate is concentrated, the residue is treated with dilute ammonia solution and the mixture is extracted with methylene chloride. The organic phases are washed with water, dried over Na$_2$SO$_4$ and concentrated. The residue is taken up in 2 ml of acetonitrile. The solution is left to crystallise for 24 hours and the crystals formed are filtered off. These crystals consist of 46 mg of the laevorotatory enantiomer of the compound (5), of optical rotation $[\alpha]_D^{20} = -77.9°$ (c=0.1; AcOH).

Melting point = 196°–197° C.

The filtrate is concentrated and the residue is crystallised from 3 ml of MeOH. This yields 36 mg of the dextrorotatory enantiomer of the compound (5), of optical rotation $[\alpha]_D^{20} = +77.9°$ (c=0.1; AcOH).

Melting point = 195°–197° C.

2. (+)-Vincamine 6 ml of 37% strength formaldehyde solution and 5 ml of titanium (III) chloride solution (15% strength) are introduced into a round-bottomed flask. The mixture is heated to 60° C. A solution of 310 mg of the (+)-enantiomer of the compound (5) in 2 ml of acetone and 2 ml of acetic acid is added. The mixture is left to react for 30 minutes at 55°–60° C. It is treated with NaNO$_2$. A stream of argon is passed through for 3 minutes. Extraction is carried out several times with methylene chloride. The extracts are concentrated and the residue is taken up in ice and an ammoniacal solution. The mixture is filtered and the product is recrystallised from methanol in the presence of sodium methylate. This yields (+)-vincamine which melts at 227°–230° C.

$[\alpha]_D^{20} = -41°$ (c=1; pyridine).

3. (−)-Vincamine

The laevorotatory enantiomer of the compound (5) is reacted under the same conditions as in paragraph 2 and this yields (−)-vincamine.

Melting point = 228°–230° C.

$[\alpha]_D^{20} = -41.4°$ (c=1; pyridine).

I claim:

1. A process for the preparation of vincaminic acid derivatives of formula

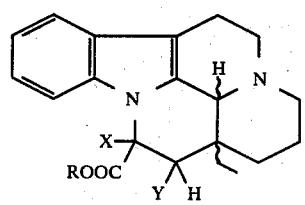

(A)

in which R is methyl or ethyl and X is hydroxy or hydrogen and Y is hydrogen or X and Y together form a carbon to carbon double bond, which process is characterised in that the enamine (1)

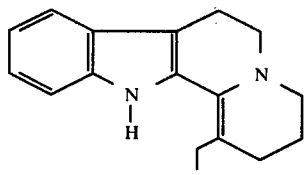
(1)

is reacted with the (2,4-dinitrophenyl)-hydrazone of ethyl or methyl bromopyruvate (2)

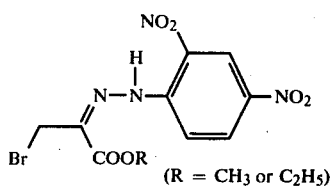
(2)

(R = CH₃ or C₂H₅)

and then either the protective group is removed from the compound (3)

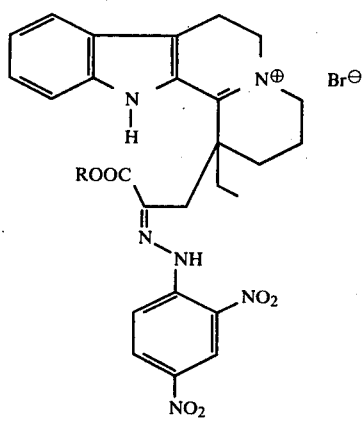
(3)

in order to obtain the cyclised compound (4)

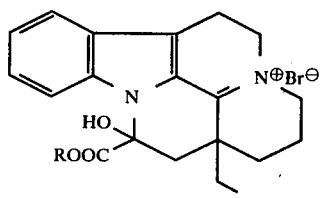
(4)

which is reduced in order to obtain the compound (6)

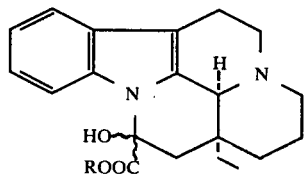
(6)

or the compound (3)

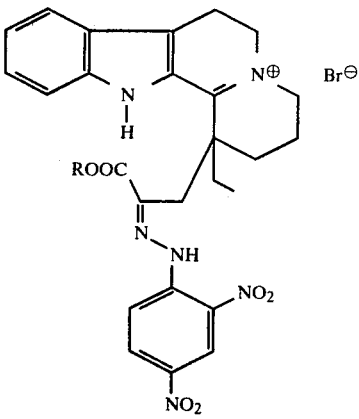
(3)

is reduced in order to obtain the compound (5)

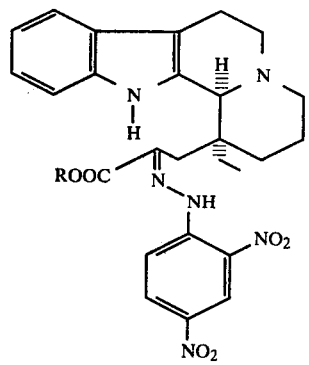
(5)

if desired compound (5) is resolved to produce either optically isomeric form thereof, and the compound (5) is treated as follows:

either (a) the protective group is removed therefrom in order to obtain the cyclised compound

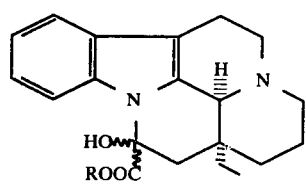
(6)

which, if desired, is transesterified, if R is C₂H₅ to give vincamine (7)

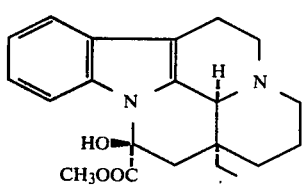
(7)

or (b) it is reacted, in formic acid, either with an about 15% strength solution of titanium (III) chloride in order to obtain ethyl apovincaminate (8,R=C₂H₅) or apovincamine (8,R=CH₃), or with an about 30% strength solution of titanium (III) chloride in order to obtain ethyl deoxyvincaminate (9,R=C$_2$H$_5$) or deoxyvincamine (9,R=CH$_3$)

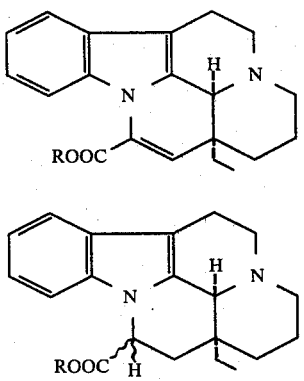

respectively.

2. A process according to claim 1, which process is characterised in that the compound (3) is prepared in ethyl acetate at ambient temperature, the protective group is removed from the compound (3) using sodium borate and hydrochloric acid in a mixture of acetonitrile and water at ambient temperature, the compound (4) is reduced with zinc or Raney nickel in acetic acid, and, if desired, the compound (6) is transesterified to give (±)-vincamine by heating in methanol at the reflux temperature in the presence of an alkali metal methylate.

3. A process according to claim 1, characterised in that the compound (3) is prepared in ethyl acetate at ambient temperature, the compound (3) is reduced to give the compound (5) using an alkali metal hydride in an acid medium in a mixture of the solvents methanol and acetonitrile, the protective group is removed from the compound (5) with titanium (III) chloride in a solvent, containing formaldehyde and hydrochloric or acetic acid, at a temperature of from 20° to 140° C., and, if desired, the compound (6) is transesterified to give (±)-vincamine by heating in methanol at the reflux temperature in the presence of an alkali metal methylate.

4. A process according to claim 1, characterised in that the compound (3) is prepared in ethyl acetate at ambient temperature, the compound (3) is reduced to give the compound (5) using an alkali metal hydride in an acid medium in a solvent and the compound (5) is then reacted with an about 15% strength solution of titanium (III) chloride in order to obtain ethyl (±)-apovincaminate or (±)-apovincamine.

5. A process according to claim 1, characterised in that the compound (3) is prepared in ethyl acetate at ambient temperature, the compound (3) is reduced to give the compound (5) using an alkali metal hydride in an acid medium in solvents, such as methanol or acetonitrile, and the compound (5) is then reacted with an about 30% strength solution of titanium (III) chloride in order to obtain ethyl (±)-deoxyvincaminate or (±)-deoxyvincamine.

6. A process according to claim 1 for the preparation of (+)- or (−)-vincamine which process is characterised in that the compound (5) in which R=CH$_3$ is resolved with an optically active acid, into its optical isomers, and either isomer is reacted with titanium (III) chloride in order to obtain (+)-vincamine or (−)-vincamine.

7. Process according to claim 6, characterised in that the optically active acid is dibenzoyl-L-tartaric acid.

* * * * *